United States Patent
Watanabe

(10) Patent No.: US 6,814,028 B2
(45) Date of Patent: Nov. 9, 2004

(54) MILKING APPARATUS FOR LABORATORY ANIMALS

(75) Inventor: Toshi Watanabe, Kanagawa (JP)

(73) Assignee: Nihon University, School Juridical Person, Tokyo (JP)

( * ) Notice: Subject to any disclaimer, the term of this patent is extended or adjusted under 35 U.S.C. 154(b) by 0 days.

(21) Appl. No.: 10/220,818

(22) PCT Filed: Dec. 21, 2000

(86) PCT No.: PCT/JP00/09112

§ 371 (c)(1),
(2), (4) Date: Sep. 6, 2002

(87) PCT Pub. No.: WO01/67064

PCT Pub. Date: Sep. 13, 2001

(65) Prior Publication Data

US 2003/0051668 A1 Mar. 20, 2003

(30) Foreign Application Priority Data

Mar. 7, 2000 (JP) ........................ 2000-061552

(51) Int. Cl.[7] .................................................. A01J 5/04
(52) U.S. Cl. ................................................... 119/14.44
(58) Field of Search .......................... 119/14.01–14.03, 119/14.08, 14.44

(56) References Cited

U.S. PATENT DOCUMENTS

| | | | | |
|---|---|---|---|---|
| 3,189,002 A | * | 6/1965 | Noorlander | 119/14.07 |
| 4,011,838 A | * | 3/1977 | Nordegren et al. | 119/14.08 |
| 4,034,711 A | * | 7/1977 | Bender et al. | 119/14.11 |
| 4,190,021 A | * | 2/1980 | Reisgies | 119/14.44 |
| 5,052,341 A | * | 10/1991 | Woolford et al. | 119/14.2 |
| 5,419,280 A | * | 5/1995 | Musha et al. | 119/14.28 |
| 5,720,236 A | * | 2/1998 | Carrano et al. | 119/14.46 |
| 5,857,424 A | * | 1/1999 | Johnston | 119/14.47 |
| 5,860,388 A | * | 1/1999 | Tan et al. | 119/14.44 |
| 6,176,200 B1 | * | 1/2001 | Petterson | 119/14.47 |
| 6,439,156 B1 | * | 8/2002 | Fleischman | 119/14.33 |

FOREIGN PATENT DOCUMENTS

| | | |
|---|---|---|
| JP | 32-2077 | 3/1957 |
| JP | 49-133162 | 12/1974 |
| JP | 58-74943 | 5/1983 |
| JP | 62-72643 | 5/1987 |
| JP | 7-31312 | 2/1995 |
| WO | 96/25036 | 8/1996 |

OTHER PUBLICATIONS

International Search Report.
McKenzie, Jr., W.N. et al, "A Modified Device for Collecting Milk from Guinea Pigs" Journal of Dairy Science, vol. 62, No. 9, Sep. 1979, pp. 1469–1470.
International Search Report of PCT/JP00/09112 dated Feb. 23, 2000.
McKenzie, JR., W.N. et al., "A Modified Device for Collecting Milk from Guinea Pigs" Journal of Dairy Science, vol. 62, No. 9, Sep. 1979, pp. 1469–1470.

* cited by examiner

*Primary Examiner*—Thomas Price
(74) *Attorney, Agent, or Firm*—Sughrue Mion, PLLC

(57) ABSTRACT

A milking apparatus for laboratory animals enables a milking operation to be performed on a laboratory animal (such as a rat) by a single experimenter, and also enables universal milking data to be obtained that is not influenced by individual difference among experimenters. A teat cup enables milking to be performed directly from the nipple of a relatively small and prolific laboratory animal such as a rat and mouse. The invention provides useful means for clarifying the influence of harmful extrinsic substances on living organisms via milk.

The apparatus comprises a milk-collecting container 10 whose inside can be kept blocked from the outside air, two, i.e., a first and second, tubes 12, 13 inserted into the milk-collecting container in a communicated manner, and a teat cup 20 replaceably mounted on the other end of the first tube 12. The other end of the second tube 13 is provided with a pressure switching means such as electromagnetic valves 33A and 33B that can switch the state inside the second tube 13 between a state where the inside is connected to the negative pressure creating source 35 and another state where it is opened to the atmosphere.

13 Claims, 8 Drawing Sheets

MILKING APPARATUS FOR LABORATORY ANIMALS

TECHNICAL FIELD

The present invention relates to a milking apparatus for laboratory animals, and more particularly to a milking apparatus suitable for relatively small and prolific laboratory animals such as, e.g., rats and mice.

BACKGROUND ART

Recent years have seen the presence of substances responsible for environmental pollution and harmful to living bodies, such as carcinogenic substances and endocrine disrupting (chemical) substances, becoming a global problem. It is of concern how these harmful substances may affect living bodies through milk such as breast milk. If it becomes possible to collect milk from laboratory animals such as rats and mice by a simpler method, such a method would be a useful means of clarifying the influence of the above-mentioned harmful extrinsic substances on living bodies.

However, relatively small and prolific laboratory animals such as rats and mice have a small nipple and produce only a small amount of milk, and for this reason there has not been proposed an effective milking apparatus. For example, it is difficult to collect milk directly from the nipple of a rat. In laboratories, therefore, milk is usually collected from the stomach of a baby rat that has been fed with milk. In the milk collected from the stomach, however, the milk component may potentially be broken down and digested by having been mixed with saliva and gastric juice and stirred. It is, therefore, an open question whether such milk can be called authentic milk.

C. T. Rodgers proposes (Laboratory Animals (1995) 29, 450–455) an apparatus for directly milking a rat, as shown in FIG. 11. In this apparatus, a milk-collecting test tube 61 is arranged in a glass container 60, which is then closed by a lid 62. One end of a flexible tube 63 is inserted into the milk-collecting test tube 61 in a communicated manner. The flexible tube 63 extends through the lid 62 to the outside of the glass container 60, and its front end is attached to a teat cup 64 made of silicon. The lower part of the glass container 60 is provided with two openings 65, 66, to the latter of which is attached a tube connected to a negative pressure creating source (not shown).

When a rat is milked by using this apparatus, vacuum is drawn from one opening 66 by continuously operating the negative pressure creating source, while the experimenter closes and opens the other opening 65 by a finger to thereby produce a pulsation. The pulsation is transmitted to the teat cup 64 via the flexible tube 63, and milk is collected by the teat cup 64 applied to the nipple of the rat. The above mentioned paper reports that 1.0–1.5 ml of milk was collected, by using the above apparatus, from all the nipples of mother rats on the fourteenth day of lactation.

The above milking apparatus shows that it is possible to directly milk from the nipple of a rat and the apparatus is therefore useful. This milking apparatus, however, requires two experimenters to operate. Namely, one experimenter must put the mother rat in place by one hand and operate the teat cup 64 by the other. The other experimenter must open and close the front end of the pressure-reducing opening 65 with his or her index finger in order to produce a pulsation. Further, since the beat is produced by the finger operation by the experimenter, errors tend to arise due to differences between individual experimenters. Thus, it is not easy to obtain data such as universal milked amount. Moreover, there has been no concrete report about the shape of the teat cup, and this remains an issue to be addressed in the future for better milking.

Accordingly, it is an object of the present invention to provide a novel milking apparatus for laboratory animals by which a single experimenter can perform a milking operation and which makes it possible to obtain milking data universally not influenced by individual differences among experimenters. It is another object of the present invention to provide a novel teat cup particularly suitable for a milking apparatus for laboratory animals.

DISCLOSURE OF THE INVENTION

The present invention provides a milking apparatus for laboratory animals comprising a milk-collecting container whose inside can be kept shut from the outside air, a first and second tubes having one of their ends inserted into an upper part of the milk-collecting container in such a manner as to communicate with the inside of the container, a teat cup replaceably attached to the other end of the first tube, a negative pressure creating source attached to other end of the second tube, and a pressure switching means for switching, in a pulsed manner, the state inside of the second tube between an atmospheric pressure state and a negative pressure state created by the negative pressure creating source.

In this milking apparatus for laboratory animals, the negative pressure creating source is continuously operated, and a negative pressure is developed inside the second tube by connecting it with the negative pressure creating source by means of the pressure switching means. The negative pressure is directly transmitted from the milk-collecting container to the teat cup via the first tube. As the pressure switching means opens the second tube to the atmosphere and the atmospheric pressure develops therein, the teat cup is brought under the atmospheric pressure. Thus, by operating the pressure switching means in a pulsating or cyclical manner, a continuous pulsation develops at the front end of the teat cup.

In that state, the experimenter can perform a required milking operation by putting the mother rat in place with one hand while applying the teat cup to the nipple of the laboratory animal with the other hand. This means that a continuous milking operation can be performed by a single experimenter. This is a great advantage provided by the present invention. Since the repetition of the negative pressure and the atmospheric pressure directly acts on the nipple of the laboratory animal via the teat cup, the milking operation can smoothly proceed even in the case of a small laboratory animal such as a rat.

The milk obtained from the laboratory animal by the pulsation of the teat cup is collected at the lower portion of the milk-collecting container via the first tube. For structural reasons, the milk collected in the milk-collecting container does not flow into the second tube, thereby preventing the pressure switching means and the negative pressure-creating source from being subjected to operational failure.

In the milking apparatus for laboratory animals according to the present invention, the negative pressure creating source may be of any type. In a preferred embodiment, however, a vacuum pump and a pressure controller for controlling the pressure inside the second tube are used as a single unit in constructing the milking apparatus for laboratory animals. By using a negative pressure tank such as an accumulator, a stable pulsation can be obtained.

Alternatively, a negative pressure creating means using, as the operating source, the amount of motion of a fluid (such as tap water, air, vapour and the like) flowing at a substantially stable flow rate, such as an aspirator, may be used. In this case, the negative pressure can be easily adjusted to a desired value by adjusting the flow rate of the fluid by opening or closing the tap without using the pressure controller, thereby simplifying the apparatus.

The pressure switching means may comprise an open/close valve such as a two-way electromagnetic valve capable of switching the state inside the second tube between a state where the inside is opened to the atmosphere and a state where the inside is blocked therefrom, with the second tube being connected to the negative pressure source at all times. In another embodiment, the pressure switching means may comprise a first open/close valve for connecting and disconnecting the second tube to and from the negative pressure source and a second open/close valve for switching the state inside the second tube upstream of the first open/close valve between a state where the inside is opened to the atmosphere and another state where the inside is blocked therefrom. In the latter case, too, an open/close valve such as a two-way electromagnetic valve is preferably used. In a further embodiment, an open/close valve of the pulsator valve type conventionally used in cow milking apparatus may be advantageously used.

In the case of using an electromagnetic valve, by providing a computer-controlled control means for controlling the open/close timing of each electromagnetic valve, a stable milking operation can be performed, and this also makes it possible to milk a variety of laboratory animals with the same apparatus under optimum conditions. In addition, in the present invention, the teat cup is adapted to be replaceably mounted on one end of the first tube, so that a teat cup with an optimum shape for a given laboratory animal to be milked can be easily selected and used.

Preferably, the teat cup comprises a top surface portion (liner) having an insertion hole into which the nipple of the laboratory animal is to be inserted, and an outer fitting portion to be fitted with the first tube, the outer fitting portion extending from the periphery of the top surface portion. At least those portions of the top surface portion near the insertion hole are provided with softness and flexibility such that, during milking, they can deform inwardly when a negative pressure develops inside the first tube and return to their original shape when the atmospheric pressure is returned therein.

In the teat cup of this shape, the insertion hole deforms when the top surface portion (i.e., the portion that comes into direct contact with the nipple and udder during milking) deforms inwardly when at negative pressure (milking period), when milk is sucked from the nipple. When at atmospheric pressure (resting period), it returns to its original posture. Such deformation of the top surface portion can provide the same effect as that of stimulating the nipple of the mother by the offspring of the laboratory animals, so that an effective milking operation can proceed.

Experiments show that the above effect can be enhanced by selectively or additionally adopting the features of: making an internal circumferential surface of the insertion hole of the teat cup inclined such that the diameter of the insertion hole becomes smaller towards the first tube with which the teat cup is fitted; forming cuts radially on the teat cup near the insertion hole; and providing a front-end portion of the first tube where the teat cup is mounted with an inclination such that the diameter of the first tube becomes greater towards the teat cup side.

In the experiments conducted by the inventors, in the case of a rat as a laboratory animal, a maximum amount of milk was obtained when a negative pressure of about −210 mmHg, preferably about −150 mmHg, was created at the front end of the teat cup for a predetermined period of time during milking (suction period), though depending on the level of pressure at which the pressure switching means can operate stably. Thus, in the milking apparatus for laboratory animals according to the present invention, preferably a negative pressure in the range of from 0 mmHg to −210 mmHg, preferably from 0 mmHg to −150 mmHg, is created at the front end of the teat cup during milking.

Figure 1:
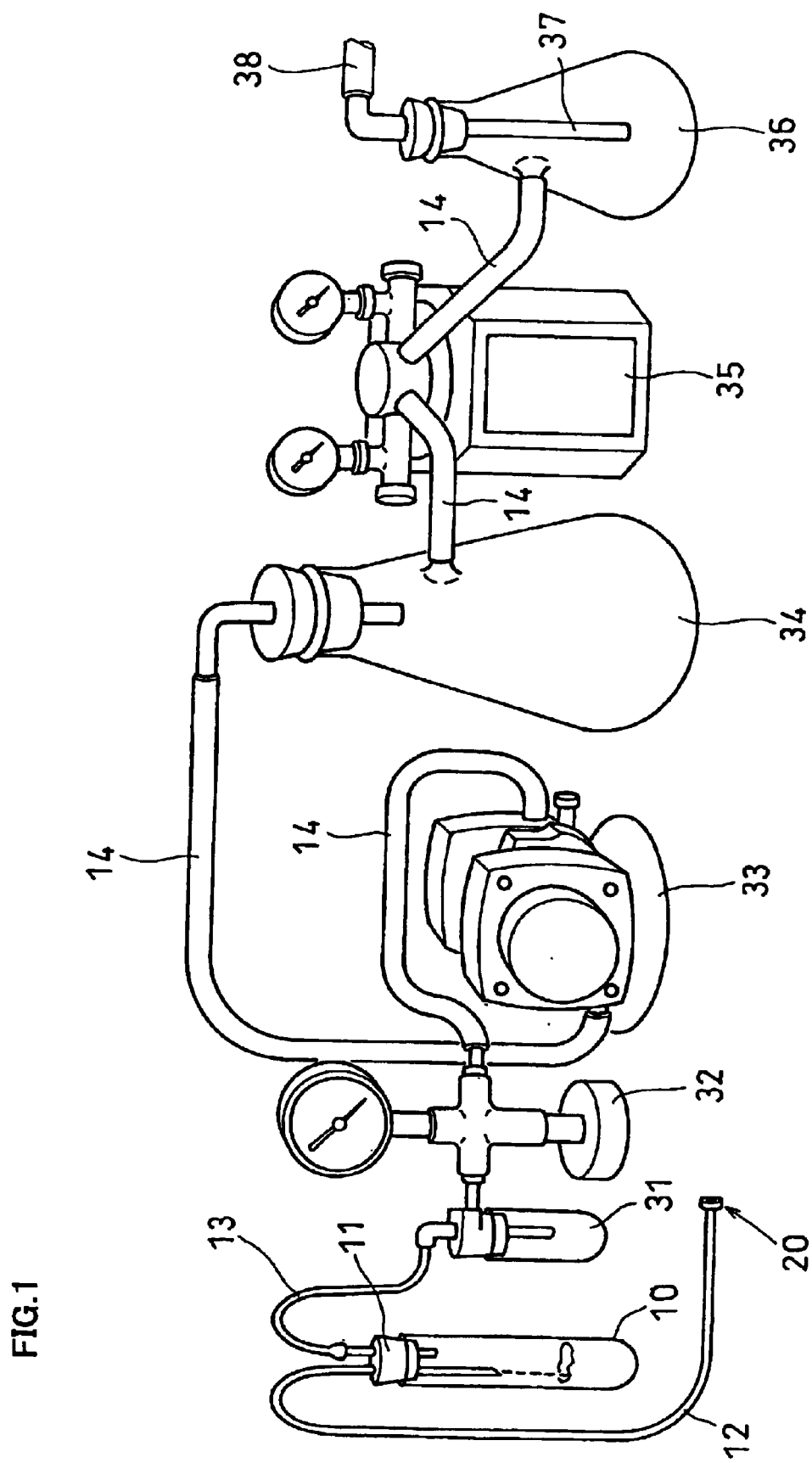
FIGS. 1–4 show different embodiments of the milking apparatus for laboratory animals according to the present invention adapted for milking rats.

| In the drawings: | |
|---|---|
| 10 | test tube to be used as a milk-collecting container |
| 11 | sealing plug |
| 12 | first tube |
| 13 | second tube |
| 20 | teat cup |
| 31 | backflow prevention valve |
| 32 | vacuum meter |
| 33 | sliding-valve type pulsator valve |
| 33A, 51, 55 | electromagnetic valve |
| 34 | filtering jar to be used as a pressure-control tank |
| 35 | vacuum pump with a pressure-control valve |
| 36 | filtering jar to be used as a silencing means |
| 40 | aspirator to be used as a negative-pressure source |
| 50 | electromagnetic valve open/close control means (computer) |

BEST MODE OF CARRYING OUT THE INVENTION

Hereafter several embodiments of the milking apparatus for laboratory animals according to the present invention will be described. FIG. 1 shows an example of the milking apparatus for laboratory animals according to the present invention which is assembled as a milking apparatus for rats. A sealing plug 11 is attached to a test tube 10 which functions as a milk-collecting container. A first tube 12 and a second tube 13 are connected via glass tubes inserted in the sealing plug 11 in such a manner as to communicate with the inside of the test tube 10. In this example, the first tube 12 and the second tube 13 are formed by plastic tubes, but they may be silicon tubes. The other end of the first tube 12 is attached to a teat cup 20 in a replaceable manner. This cup will be described later.

The other end of the second tube 13 is connected to one side of a sliding-valve type pulsator valve 33 via a backflow prevention valve 31 made of hard glass and a vacuum meter 32. The other side of the pulsator valve 33 is connected, via a filtering jar 34 which functions as a pressure-control tank or an accumulator, to a vacuum pump 35 with a pressure-control valve. Further, in order to eliminate the operating noise of the vacuum pump 35, the exhaust side of the vacuum pump is connected to an intake opening of a filtering jar 36. The filtering jar 36 is connected to an exhaust pipe 38 via an L-shaped tube 37 made of glass. Such silencing means is often required when milking a small laboratory animal such as a rat without anesthesia, so as not to excite the animal. These connections between devices are preferably made by a silicon tube 14.

In the rat milking apparatus with the above structure, after suitably adjusting the vacuum pump 35 and the pulsator valve 33 connected to the vacuum pump such that the negative pressure suitable for the milking of the rat and the atmospheric pressure pulsate at uniform intervals, the experimenter holds the rat with one hand while milking the rat by applying the front end of the teat cup 20 onto the nipple of the rat with the other hand. This milking operation can be entirely done by a single experimenter.

Figure 2:
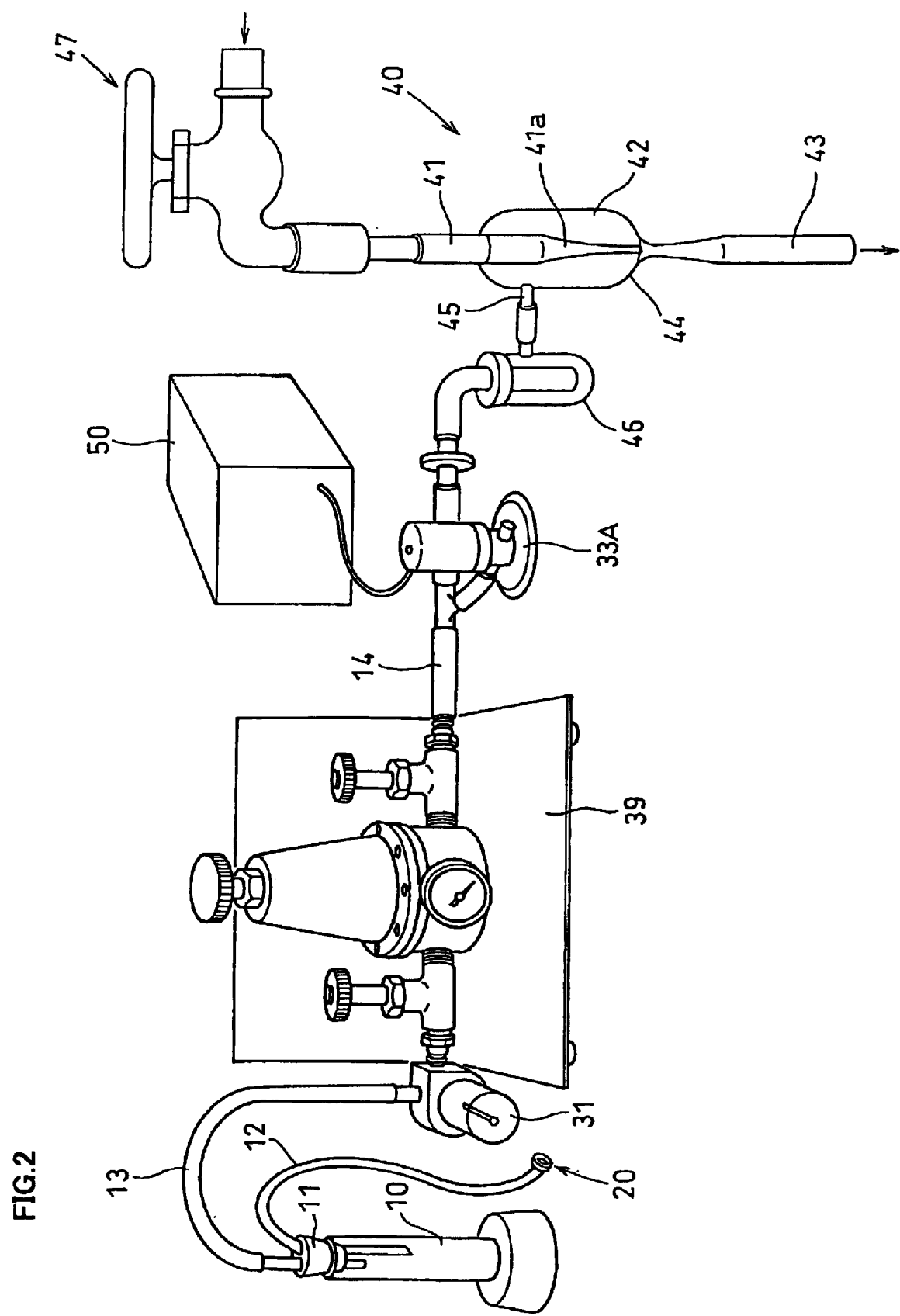

FIG. 2 shows another embodiment of the milking apparatus for laboratory animals according to the present invention. This embodiment differs from the apparatus shown in FIG. 1 in that, instead of the vacuum pump 35 as the negative pressure creating source, a negative pressure creating means (aspirator) 40 is employed. The aspirator 40 employs, as a source of operation, the amount of motion of a fluid (such as tap water) which flows substantially at a uniform flow rate. Further, instead of the pulsator 33, a two-way electromagnetic valve 33A whose opening and closing is controlled by a control means 50 using a computer (the control means 50 may be one well known in the art and so its description is omitted). The above-mentioned other end of the second tube 13 is connected, via the backflow prevention valve 31 and vacuum controller 39, to an intake side of the aspirator 40. The electromagnetic valve 33A is disposed between the vacuum controller 39 and the aspirator 40, such that the inside of the second tube 13 and device-connecting tube 14 can be switched between a state where it is connected to the aspirator 40 and another state where it is opened to the atmosphere.

The aspirator 40 is as known in the art and equipped with a conduit pipe 41 and a drainage pipe 43 having an expanded portion 42 at the front end for accommodating an ending 41a of the conduit pipe 41. Negative pressure is created within the expanded portion 42 by causing nozzle suction between a reduced-diameter portion 44 of the expanded portion 42 of the drainage pipe 43 and the ending 41a of the conduit pipe 41. The inside of the expanded portion 42 is connected, via a branch pipe 45 formed thereon and the backflow prevention valve 46, to the second tube 13 (connecting tube 14).

Since this embodiment does not employ a vacuum pump, the apparatus generates less noise and can be made smaller in size. By adjusting the vacuum controller 39, a desired negative pressure can be easily obtained. When, as shown, tap water is used as the fluid for the operation of the aspirator 40 in a laboratory, for example, the negative pressure can be easily controlled by adjusting the degree of opening of a tap 47 as well. Further, the adoption of the electromagnetic valve 33A and the control means 50 for controlling the opening and closing of the valve enables a pulsation with desired intervals to be obtained easily and thus makes it easier to deal with a variety of laboratory animals in an appropriate manner.

Figure 3:
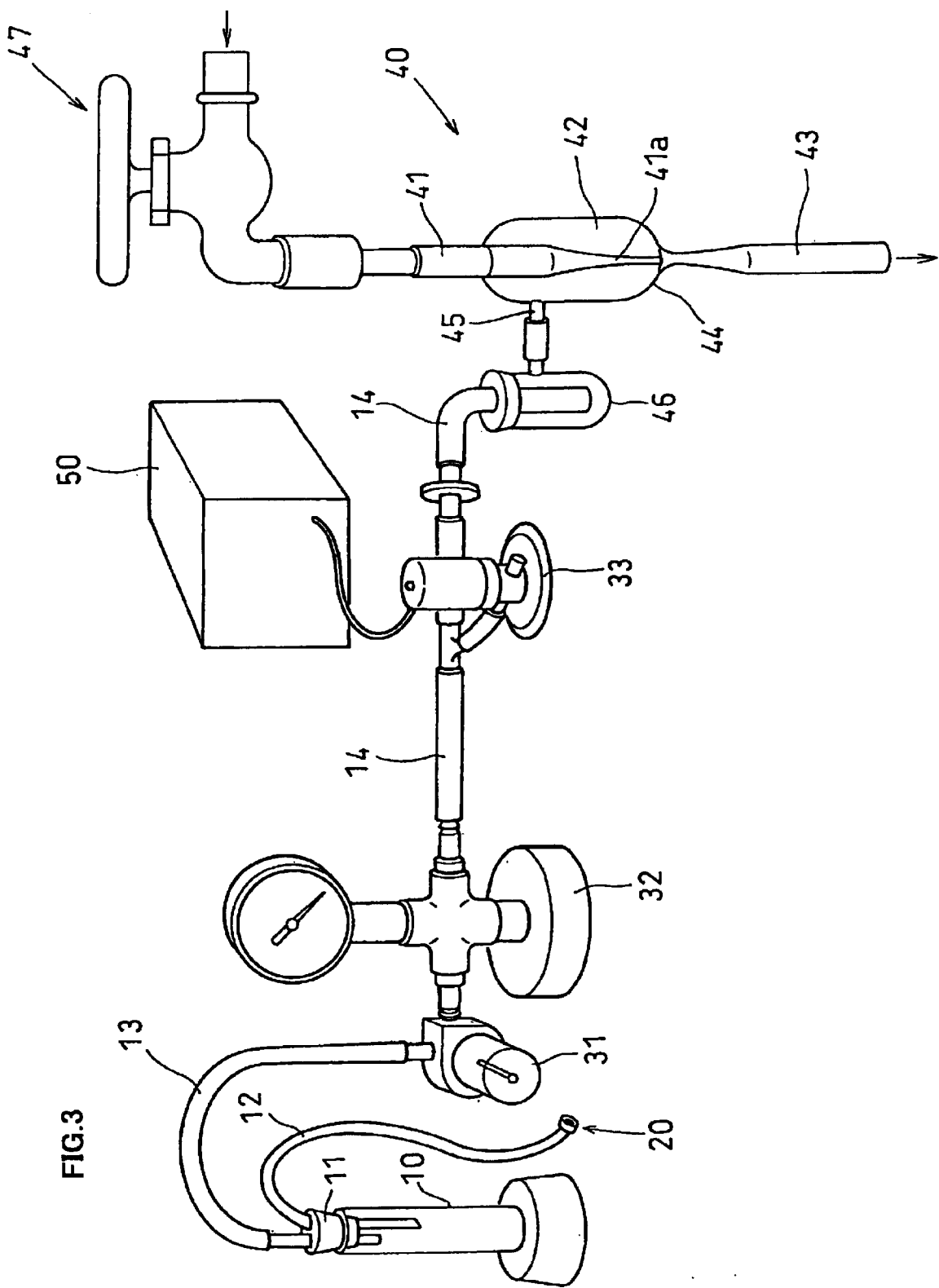

FIG. 3 shows another embodiment of the milking apparatus for laboratory animals according to the present invention. In this example, the vacuum controller 39 is removed from the apparatus of FIG. 2 and there is only the vacuum meter 32. In this case, too, any desired negative pressure necessary for milking experiments can be easily obtained by controlling the degree of opening of the tap 47 connected to the aspirator 40.

Figure 4:
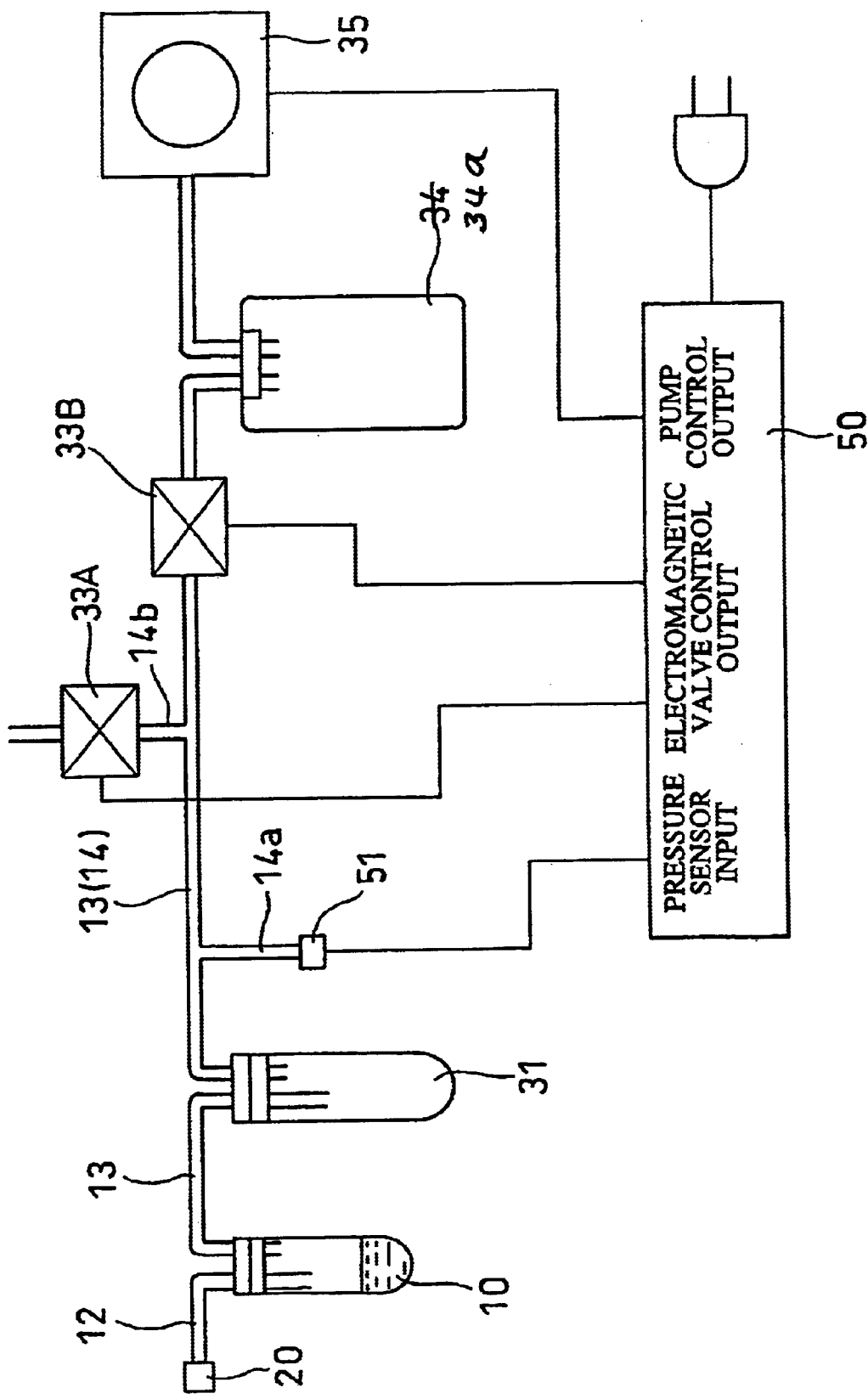

It is of course possible to replace, in the milking apparatus of FIG. 1, the pulsator 33 with an electromagnetic valve and the control means 50 for controlling the valve's opening and closing as shown in FIGS. 2 and 3. FIG. 4 schematically shows an example of the milking apparatus of that type, in which a first branch pipe 14a has a pressure sensor 51 while a second branch pipe 14b provided further downstream has a first two-way electromagnetic valve 33A. The first two-way electromagnetic valve 33A can be opened to open the second branch pipe 14b to the atmosphere. A second tube 13 has a second two-way electromagnetic valve 33B downstream of the second branch pipe 14b. By opening this valve, the other end of the second tube 13 can be communicated to a negative pressure tank 34a which functions as a pressure-control tank or an accumulator. The negative-pressure tank 34a is connected to the vacuum pump 35 and maintained at a negative pressure.

A computer 50 is connected such that information can be transmitted among the pressure sensor 51, the first and second electromagnetic valves 33A, 33B, and the vacuum pump 35. The computer 50 controls the input of pressure information from the pressure sensor 51, control output for the opening and closing timings of the first and second electromagnetic valves 33A, 33B, and operation control output for the vacuum pump 35.

An example of the operation of the milking apparatus will now be described. The vacuum pump 35 is operated while the first and second electromagnetic valves 33A, 33B are closed, such that a negative pressure is created in the negative pressure tank 34a. After a predetermined pressure is established, the second electromagnetic valve 33B is opened. As a result, the air inside the second tube 13 is drawn into the negative pressure tank 34a, thereby creating a predetermined negative pressure (set pressure) with respect to the atmospheric pressure. At that point in time, the second electromagnetic valve 33B is closed, thereby establishing and maintaining the set negative pressure state in the second tube 13 (i.e., suction from the teat cup is performed).

The above state is maintained for a predetermined period of time and then the first electromagnetic valve 33A is opened. This opens the inside of the second tube 13 to the atmosphere, so that the pressure returns to the atmospheric pressure. After maintaining this state for a predetermined period of time, the second electromagnetic valve 33B is again opened. Thereafter, this cycle is repeated a set number of times, thus proceeding with a desired milking operation. If, during the suction step, a minimum value of the set negative pressure is reached, the second electromagnetic valve 33B is temporarily opened to thereby re-suck and bring the pressure back to the set value.

Figure 5:
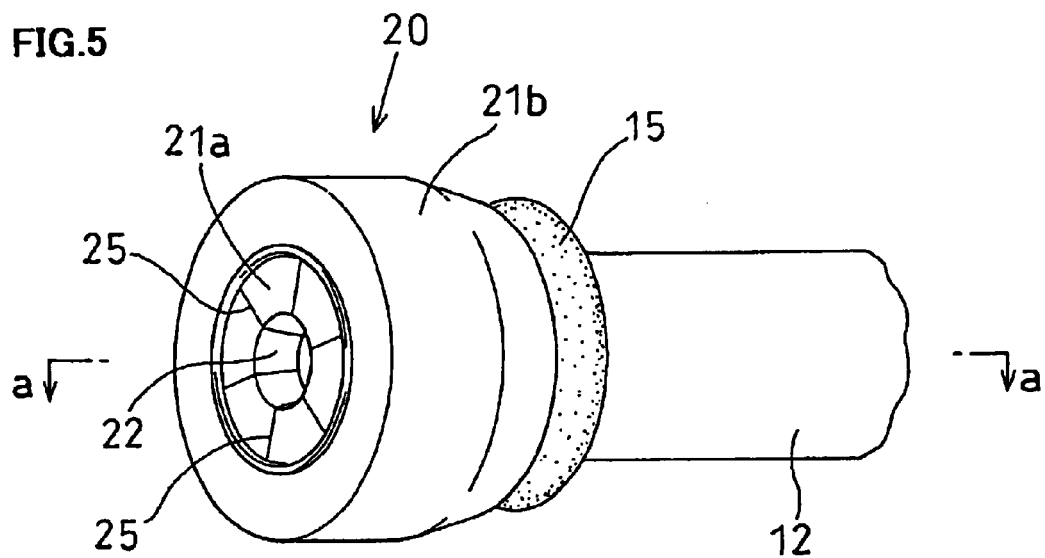
FIG. 5 shows a perspective view for the explanation of an embodiment of the teat cup according to the present invention as attached to a tube.
Figure 6:
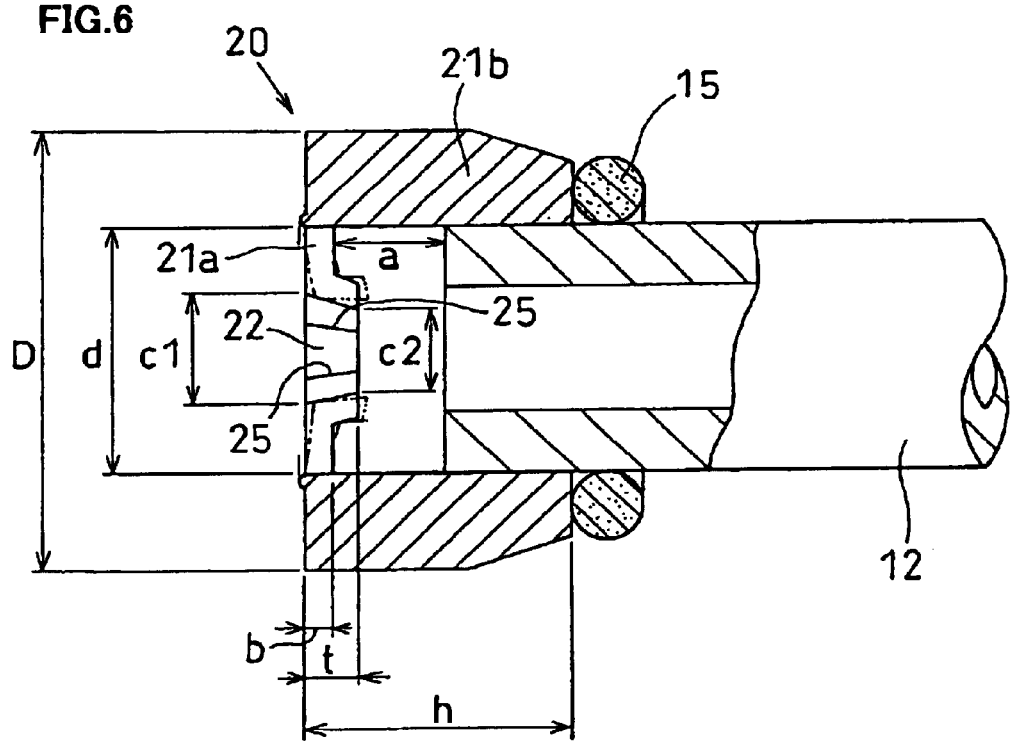
FIG. 6. shows a sectional view taken along the line a—a of FIG. 5.

Next, the teat cup used in the above apparatus will be described in detail. FIG. 5 shows a perspective view of an embodiment of the teat cup 20, which is connected to the front end of the first tube 12. FIG. 6 shows a sectional view taken along the line a—a of FIG. 5. In this example, the first tube 12 is about 2 mm in internal diameter and about 4 mm in external diameter. A silicon O-ring 15 (about 2 mm in internal diameter and about 1 mm in thickness) is fixed with glue at about 2 mm from the front end of the first tube 12, for the purpose of positioning the teat cup 20. The teat cup 20 is made of soft rubber (such as silicon rubber) and generally cylindrically shaped with a front end closed by a top surface portion (liner) 21a. It has an internal diameter d=about 4 mm, an external diameter D=about 7 mm, and a height h=about 4 mm. In this example, as shown, a gap of about 1.6 mm is formed between the back surface of the top surface portion 21a and the front end of the first tube 12 by inserting the front end of the first tube 12 into an outer fitting portion 21b of the teat cup 20.

The top surface portion 21a of the teat cup 20 functions as a liner with which the nipple and udder of a mother rat come into direct contact and has a thickness b=about 0.4 mm. A center portion of the teat cup 20 has an insertion hole 22 with a diameter c1=about 1.8 mm into which the nipple of the rat is to be inserted. The insertion hole 22 is about 0.8 mm in length t and is conically shaped with an enlarged diameter on its front-end side. Its rear-end diameter c2=about 1.4 mm. Further, the top surface portion 21a has six cuts 25 each extending radially from an inner circumferential edge of the insertion hole 22 and measuring about 1.3 mm in length.

In this teat cup 20, the insertion hole 22 opens up greatly during a milking period (reached vacuum degree period, suction period), as illustrated by the phantom line in FIG. 6, thereby sucking milk from the nipple. The sucked milk is stored in the test tube 10 via the first tube 12. During a resting period (a reached atmospheric pressure period, when the above-mentioned negative pressure is not present, an atmospheric pressure period/massaging period), the insertion hole 22 formed at the top surface portion 21a closes by its own resilience (i.e., back to the original posture as shown by the solid line in FIG. 6). As mentioned above, by this opening and closing action of the insertion hole 22, an effect similar to that of a baby rat sucking milk and thus stimulating the nipple and udder of the mother rat can be obtained. Thus, the action of the insertion hole 22 is very important.

Figure 7:
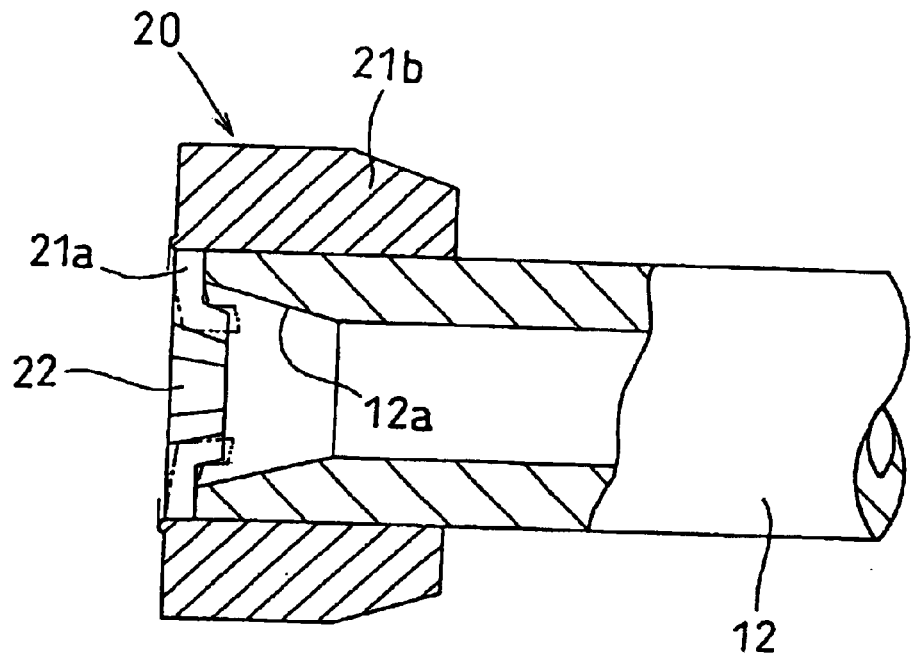
FIGS. 7 and 8 show sectional views of different examples of the manner in which the teat cup is attached to a first tube.

FIG. 7 shows a sectional view of another example of the manner in which the teat cup 20 is attached to the first tube 12. Here, the teat cup 20 is similar to that shown in FIGS. 5 and 6 except that a front-end portion of the first tube 12 to which the teat cup is to be attached is formed with an inclined surface 12a (preferably with an inclination of about 15°) such that the diameter of the first tube 12 becomes larger towards the side of the teat cup 20. The thus inclined front-end portion reaches as far as the back surface of the top surface portion 21a of the teat cup 20, in contrast to the example of FIG. 6. In this case, too, since the inclined surface 12a is formed at the front end of the fist tube 12, the opening and closing action of the insertion hole 22 proceeds in the same manner as that shown in FIGS. 5 and 6. Since this example does not require the O-ring 15, the structure can be advantageously simplified.

Figure 8:
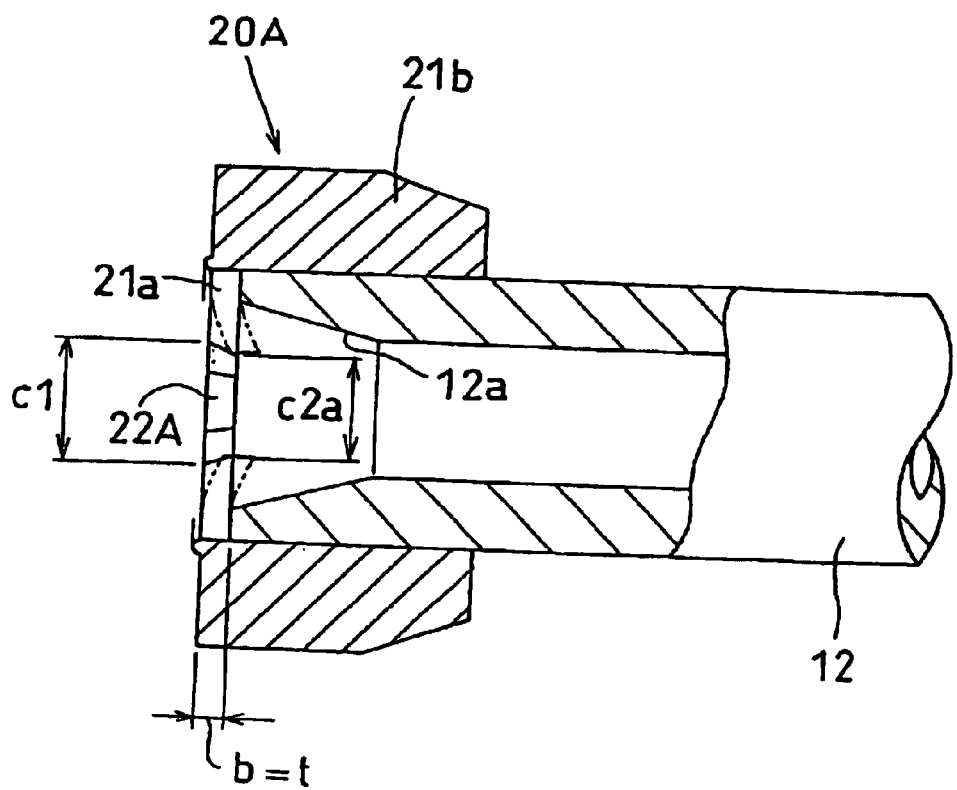

FIG. 8 shows a sectional view of another example of the manner in which the teat cup is attached to the first tube 12. Here, the insertion hole 22A formed in the teat cup 20A has a length t which is equal to the thickness b=0.4 mm of the top surface portion 21a. The teat cup has a diameter c1 of 1.8 mm at its front-end side and a diameter c2a of 1.5 mm at its rear-end side, and is thus conically shaped. Experiments showed that the teat cup 20A of this type, when used in combination with the first tube formed at the front end with the inclined surface 12a, was capable of providing the same opening and closing action of the insertion hole. Though not shown, the experiments also confirmed that almost identical opening and closing action can be obtained in this case without providing the six cuts 25. Presumably this is due to the result of the top surface portion 21 of the teat cup 20A extending and contracting circumferentially as well.

Figure 9:
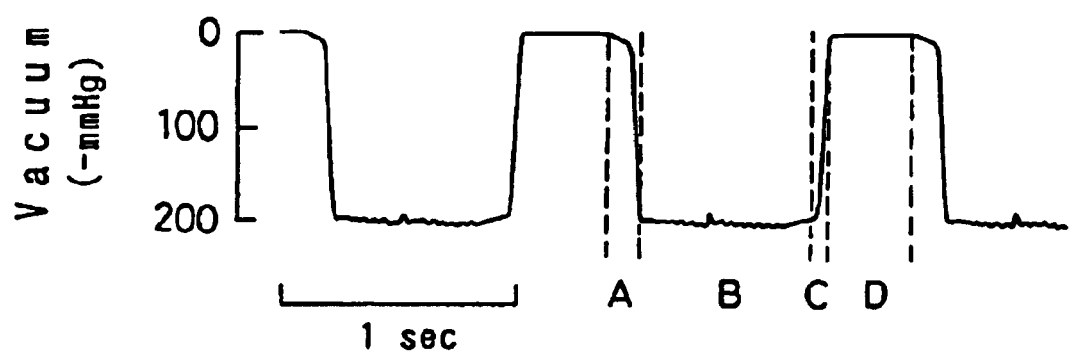
FIG. 9 shows a pulsation characteristics curve (pulsogram) of the milking apparatus for rats shown in FIG. 1.

Hereafter, an experiment is described in which a rat was milked by mounting the teat cup 20 shown in FIGS. 5 and 6 on the rat milking apparatus shown in FIG. 1. FIG. 9 shows a pulse characteristics curve (pulsogram) of the present experiment, and Table 1 shows the analysis values. When the analysis results of the pulsogram in the above rat milking apparatus were compared with those of the pulsogram in a milking apparatus for cows which is not shown, the values were within international standard values for cow milking apparatus, except for the degree of vacuum. A standard degree of vacuum in a cow milking apparatus is about −330 mmHg, in the range of from −300 mmHg to −350 mmHg. In the above milking apparatus for rats, the greatest amount of milk was obtained when the degree of vacuum was about −210 mmHg and under the conditions shown in Table 1. In FIG. 9 and Table 1, A: Transitional period (reached vacuum degree period), B: Suction period, C: Transitional period (reached atmospheric pressure period), and D: Atmospheric pressure period. A+B indicates the milking period, and C+D indicates the resting period (massaging period).

TABLE 1

| | |
|---|---|
| Degree of vacuum (-mmHg) | 210 |
| Number of pulses (min) [a)] | 46 |
| Pulsation ratio (suction period ratio) [b)] | 66 |
| A (msec) | 140 |
| B (msec) | 720 |
| C (msec) | 80 |
| D (msec) | 360 |
| A + B (msec) | 860 |
| C + D (msec) | 440 |

[a)] $60/A + B + C + D \times 1000$ = times/min
[b)] $A + B/A + B + C + D \times 100$ The details of the experiment are as follows. Eight-week-old Sprague-Dawley rats (Jcl: SD, Clea Japan Inc.) were raised under conditions of 40 to 60% humidity, 23±1° C. temperature, and 14-hours illumination (from 5 a.m. to 7 p.m.). Feed (CE-2Clea Japan Inc.) and water were freely provided. After three weeks of acclimation under these conditions, only visibly healthy rats were selected and used in the experiment. A 12-week-old female rat regularly exhibiting a sexual cycle and a male rat of similar variety were put in an aluminum cage and mated. Pregnant rats were transferred to a polyacrylic cage for delivery. Four days after delivery, the number of offsprings was randomly adjusted to four males and four females, totalling eight offsprings.

The eight offsprings were separated from their mothers at 8 a.m., 14 days after delivery when the rats lactate the most. At 4 p.m., the mothers were given a hypodermic injection of Oxytocin 1 IU (Atonin-O, Teikoku Zoki Co.,). A method of measuring the amount of milk based on weight differences in the mother rat and baby rat before and after breast-feeding was used. Twenty minutes after the injection of Oxytocin, the mother rat was anesthetized (sodium pentobarbital), and the nipple, udder and their vicinity were sterilized by 70%-alcohol cotton. After gently massaging the mammary gland with a finger, the top surface portion 21a of the teat cup 20 was made, by using one hand, to suck the nipple and milking was initiated. During the milking operation, the mammary gland was continuously gently massaged by the thumb and index finger of the other hand. Milking was possible from all of the nipples from which the eight offsprings were fed.

Table 2 shows the amounts of milk milked from all of the nipples from which the eight offsprings were fed, under the conditions of Table 1. An average amount of milk obtained from a mother rat on the fourteenth day of lactation was 3.43±1.71 g. This amount is less than the milked amount calculated from the weight differences in the mother rat and baby rat before and after breast-feeding, but is sufficient for today's chemical analysis methods.

TABLE 2

|  | Milked amount (g/mother rat) |
| --- | --- |
| Number of mother rats | 10 |
| Average ± standard deviation | 3.43 ± 1.71 |
| Range | 1.4–6.5 |

Figure 10:
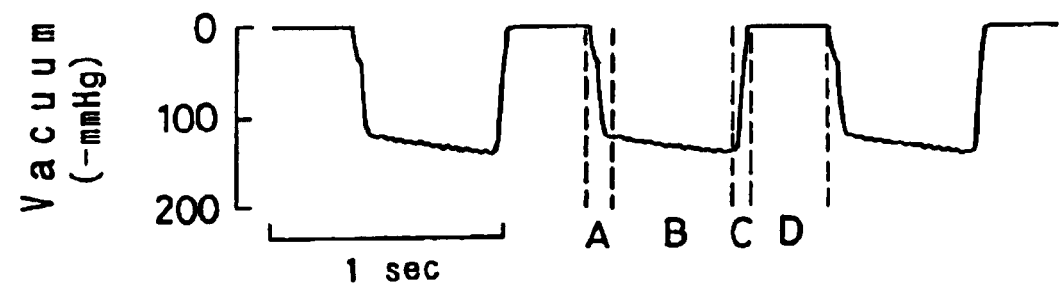
FIG. 10 shows a pulsation characteristics curve (pulsogram) of the milking apparatus for rats shown in FIG. 4.
Figure 11:
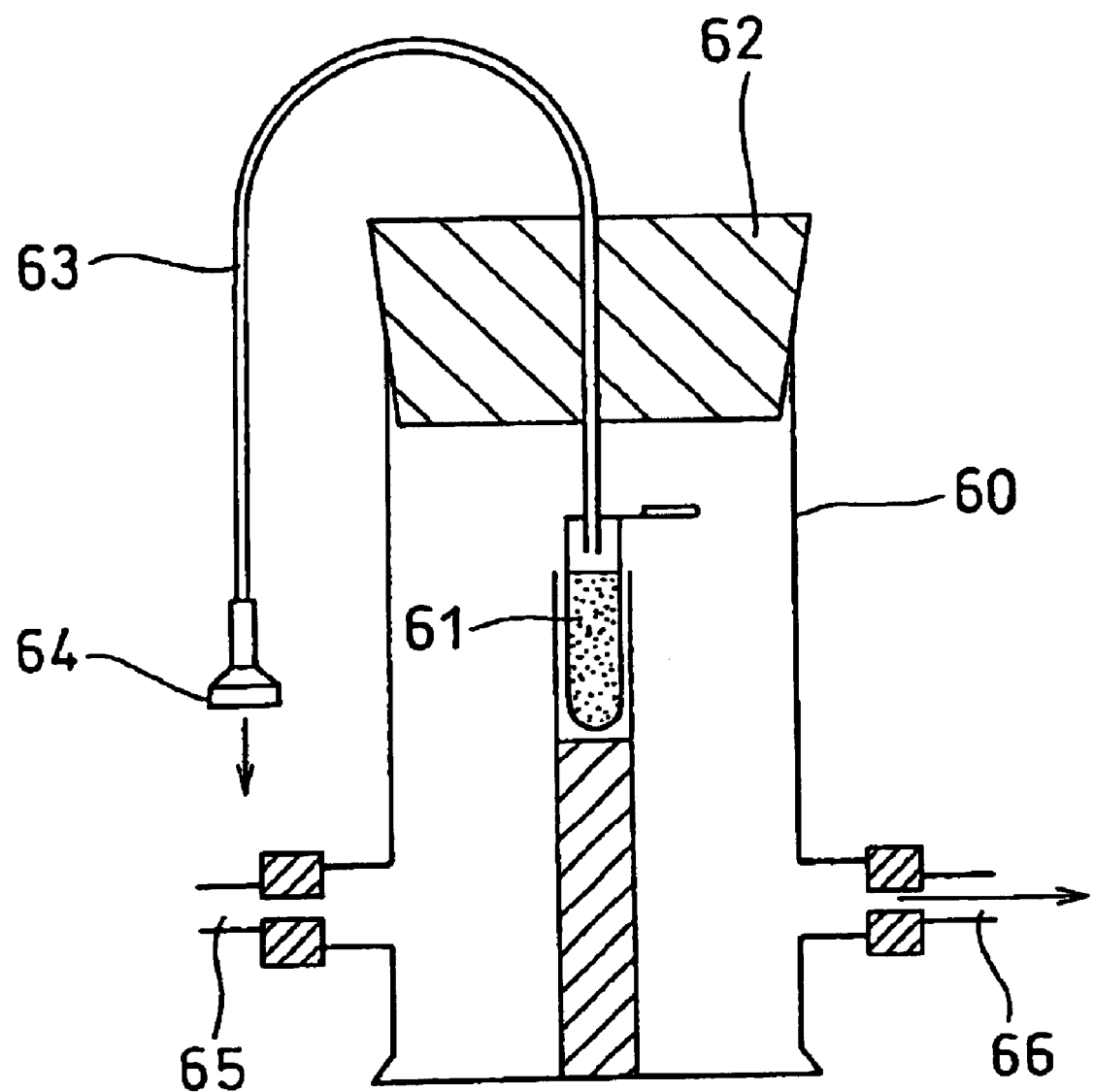
FIG. 11 is a drawing for the explanation of a milking apparatus for rats proposed by the prior art.

Similarly, another rat milking experiment was conducted by attaching the teat cup 20 shown in FIGS. 2 and 3 to the rat milking apparatus shown in FIG. 4 in the following manner. FIG. 10 shows a pulse characteristics curve (pulsogram) in the experiment, and Table 3 shows the analysis values. In the above rat milking apparatus, the greatest amount of milk was obtained when the degree of vacuum was about −140 mmHg and under the conditions of Table 3. While the greatest amount of milk was obtained at a lower degree of vacuum than in the case of the rat milking apparatus shown in FIG. 1, presumably this is due to the fact that the apparatus of FIG. 1 required a higher degree of vacuum to facilitate a proper operation of the valve necessitated by the structure of the valve. In FIG. 10 and Table 3, A: Transitional period (reached vacuum degree period)(first electromagnetic valve 33A closed, second electromagnetic valve 33B open), B: Suction period (first electromagnetic valve 33A closed, second electromagnetic valve 33 open), C: Transitional period (reached atmospheric pressure period) (first electromagnetic valve 33A open, second electromagnetic valve 33B closed), D: Atmospheric pressure period (first electromagnetic valve 33A closed, second electromagnetic valve 33B closed). A+B indicates a milking period, and C+D indicates a resting period (massaging period).

TABLE 3

| Degree of vacuum (-mmHg) | 140 |
| --- | --- |
| Number of pulses [a] | 60 |
| Ratio of pulsation [b] | 60 |
| A (msec) | 100 |

TABLE 3-continued

| B (msec) | 500 |
| --- | --- |
| C (msec) | 80 |
| D (msec) | 320 |
| A + B (msec) | 600 |
| C + D (msec) | 400 |

[a] $60/A + B + C + D \times 1000$ = times/min
[b] $A + B/A + B + C + D \times 100$ The details of the experiment were as follows. Eight-week-old Sprague-Dawley rats (Jcl:SD, Clea Japan Inc.) were raised under the conditions of 40–60% humidity, 23±1° C. temperature and 14 hours illumination (5 a.m. to 7 p.m.). Feed (CE-2Clea Japan Inc.) and water were freely provided. After three weeks of acclimation under these conditions, only visibly healthy rats were selected and used for the experiment. Twelve-week-old female rats that regularly exhibited a sexual cycle and male rats of similar variety were put in an aluminum cage and mated. Pregnant rats were transferred to a polyacrylic cage for delivery. Four days after delivery, the number of baby rats was randomly adjusted to four males and four females, totalling eight offsprings.

The eight offsprings were separated from the mothers at 8 a.m. 4, 7, 10, 14, and 18 days after delivery, and the mothers were given hypodermic injection of Oxytocin 1 IU (Atonin-O, Teikoku Zoki Co.,) at 4 p.m. A method of measuring the amount of milk based on weight differences in the mother rat and baby rat before and after breast-feeding was employed. Twenty minutes after the Oxytocin injection, the mother rats were anesthetized (sodium pentobarbital), and the nipple, udder and their vicinities were sterilized by 70%-alcohol cotton. After gently massaging the mammary gland by hand, the top surface portion 21a of the teat cup 20 was made to suck the nipple by one hand, and milking was initiated. During milking, the udder was continuously and gently massaged by the thumb and index finger of the other hand. Milking was possible from all the nipples from which the eight offsprings were fed.

Table 4 shows the amounts of milk obtained from all the nipples from which the eight baby rats were fed, under the conditions shown in Table 3. The average amount of milk obtained from the mother rats on the fourteenth day of lactation was 3.99±1.22 g, the highest amount from among the milking groups. While this amount was less than the amount of milk calculated from the weight differences in the mother rat and baby rat before and after breast-feeding, this amount is sufficient for today's chemical analysis methods.

TABLE 4

| Number of days after delivery | 4 | 7 | 10 | 14 | 18 |
| --- | --- | --- | --- | --- | --- |
| Average milked amount g[a] | 0.76 ± 0.48 | 1.66 ± 0.65 | 2.47 ± 0.67 | 3.99 ± 1.22 | 2.10 ± 0.93 |
| Range | 0.28–1.78 | 1.01–2.88 | 1.59–3.57 | 2.05–6.21 | 0.28–3.27 |
| Number of mother rats with a milked amount 0.5 g or more (%) | 66(10/15[b]) | 100(15/15[b]) | 100(15/15[b]) | 100(15/15[b]) | 80(12/15[b]) |

The values are an average milked amount ± standard deviation of 15 mother rats.
[a] Milked amount from all of the nipples
[b] Number of mother rats with a milked amount of 0.5 g or more/number of all the mother rats milked × 100%

Thus, by using the milking apparatus for laboratory animals according to the present invention, a single experimenter can perform a milking operation on a laboratory animal, and universal milking data that is not influenced by individual differences among experimenters can be obtained. By using the teat cup according to the present invention which is particularly suitable for the milking apparatus for laboratory animals, relatively small and prolific laboratory animals such as rats and mice can be directly milked from the nipple. Accordingly, the present invention can provide a useful means for revealing the influences of harmful extrinsic substances on the living bodies through milk.

What is claimed is:

1. A milking apparatus for laboratory animals, comprising:
    a milk-collecting container whose inside can be kept shut from the outside air;
    first and second tubes having one of their ends inserted into an upper part of the milk-collecting container in such a manner as to communicate with the inside of the container;
    a teat cup replaceably attached to the other end of the first tube;
    a negative pressure creating source attached to the other end of the second tube; and
    a pressure switching means disposed between the milk-collecting container and the negative pressure creating source for switching, in a pulsed manner, the state inside of the second tube between an atmospheric pressure state and a negative pressure state created by the negative pressure creating source.

2. A milking apparatus for laboratory animals according to claim 1, wherein the negative pressure creating source is a vacuum pump, the apparatus further comprising a pressure controller for controlling the pressure inside the second tube.

3. A milking apparatus for laboratory animals according to claim 1, wherein the negative pressure creating source is a negative pressure creating means having, as an operation source, the amount of motion of a fluid flowing at a substantially stable flow rate.

4. A milking apparatus for laboratory animals according to claim 1, wherein the pressure switching means, with the second tube connected to the negative pressure creating source at all times, comprises an open/close valve capable of switching the state of the inside of the second tube between a state where the inside is opened to the atmosphere and another state where the inside is blocked from the atmosphere.

5. A milking apparatus for laboratory animals according to claim 1, wherein the pressure switching means comprises a first open/close valve for connecting and disconnecting the second tube to and from the negative pressure creating source, and a second open/close valve for switching the state inside the second tube upstream of the first open/close valve between a state where the inside is opened to the atmosphere and another state where the inside is blocked from the atmosphere.

6. A milking apparatus for laboratory animals according to claim 4, wherein the open/close valve is an electromagnetic valve, the apparatus further comprising a control means for controlling the open/close timing of the electromagnetic valve.

7. A milking apparatus for laboratory animals according to claim 1, wherein the pressure switching means includes a pulsator valve.

8. A milking apparatus for laboratory animals according to claim 1, wherein the teat cup comprises a top surface portion having an insertion hole into which the nipple of a laboratory animal is to be inserted, and an outer fitting portion extending from the periphery of the top surface portion for fitting with the first tube, wherein at least portions of the top surface portion near the insertion hole are provided with softness and flexibility such that they can, at the time of milking, deform inwardly when a negative pressure develops inside the first tube and return to their original shape when the atmospheric pressure is present inside the first tube.

9. A milking apparatus for laboratory animals according to claim 8, wherein an internal peripheral surface of the insertion hole of the teat cup is inclined such that the diameter of the insertion hole is smaller towards the first tube.

10. A milking apparatus for laboratory animals according to claim 8, wherein cuts are formed radially on the top surface of the teat cup near the insertion hole.

11. A milking apparatus for laboratory animals according to claim 8, wherein a front-end portion of the first tube on which the teat cup is to be mounted is formed with an inclined surface such that the diameter of the first tube becomes larger towards the teat cup.

12. A milking apparatus for laboratory animals according to claim 1, wherein the apparatus is adapted for rats or mice.

13. A milking apparatus for laboratory animals according to claim 12, wherein a negative pressure created at the front end of the teat cup during milking is in the range of from 0 mmHg to −210 mmHg, preferably from 0 mmHg to −150 mmHg.

* * * * *